(12) United States Patent
Pal

(10) Patent No.: US 8,187,298 B2
(45) Date of Patent: May 29, 2012

(54) EMBOLIC PROTECTION DEVICE HAVING INFLATABLE FRAME

(75) Inventor: Dharmenda Pal, Wilmington, MA (US)

(73) Assignee: Cook Medical Technologies LLC, Bloomington, IN (US)

( * ) Notice: Subject to any disclaimer, the term of this patent is extended or adjusted under 35 U.S.C. 154(b) by 1008 days.

(21) Appl. No.: 11/496,880

(22) Filed: Jul. 31, 2006

(65) Prior Publication Data

US 2007/0038241 A1 Feb. 15, 2007

Related U.S. Application Data

(60) Provisional application No. 60/705,575, filed on Aug. 4, 2005.

(51) Int. Cl.
*A61M 29/00* (2006.01)
(52) U.S. Cl. .................................................. 606/200
(58) Field of Classification Search .............. 606/191, 606/192, 194, 198, 200
See application file for complete search history.

(56) References Cited

U.S. PATENT DOCUMENTS

| | | |
|---|---|---|
| 3,108,593 A | 10/1963 | Glassman |
| 3,334,629 A | 8/1967 | Cohn |
| 3,472,230 A | 10/1969 | Fogarty |
| 3,547,103 A | 12/1970 | Cook |
| 3,635,223 A | 1/1972 | Klieman |
| 3,923,065 A | 12/1975 | Nozick et al. |
| 3,952,747 A | 4/1976 | Kimmell, Jr. |
| 3,978,863 A | 9/1976 | Fettel et al. |
| 3,996,938 A | 12/1976 | Clark, III |
| 4,425,908 A | 1/1984 | Simon |
| 4,456,000 A | 6/1984 | Schjeldahl et al. |
| 4,494,531 A | 1/1985 | Gianturco |
| 4,548,206 A | 10/1985 | Osborne |
| 4,561,439 A | 12/1985 | Bishop et al. |
| 4,562,039 A | 12/1985 | Koehler |
| 4,604,094 A | 8/1986 | Shook |
| 4,619,246 A | 10/1986 | Molgaard-Nielsen et al. |

(Continued)

FOREIGN PATENT DOCUMENTS

DE 3429850 A1 2/1986

(Continued)

OTHER PUBLICATIONS

Rubicon Embolic Filter, The Next Generation of EM, Rubicon Medical, www.rubiconmed.com.

(Continued)

*Primary Examiner* — Ryan Severson
*Assistant Examiner* — David Eastwood
(74) *Attorney, Agent, or Firm* — Brinks Hofer Gilson & Lione

(57) ABSTRACT

An embolic protection device for capturing emboli during treatment of a stenotic lesion in a body vessel is provided. The device includes an inflatable frame having a deployed state and an undeployed state and a filter attached to the inflatable frame for capturing emboli. The inflatable frame includes a distal portion having a predetermined shape and extending freely to a closed distal end when the inflatable frame is in the deployed state. The filter includes a lip attached to the inflatable frame to define an open end of the filter when the inflatable frame is in the deployed state, a body extending from the lip and disposed about the inflatable frame, and a closed tail configured to capture the emboli during treatment of the stenotic lesion.

16 Claims, 3 Drawing Sheets

U.S. PATENT DOCUMENTS

| | | |
|---|---|---|
| 4,643,184 A | 2/1987 | Mobin-Uddin |
| 4,646,736 A | 3/1987 | Auth |
| 4,650,472 A | 3/1987 | Bates |
| 4,665,906 A | 5/1987 | Jervis |
| 4,669,464 A | 6/1987 | Sulepov |
| 4,688,553 A | 8/1987 | Metals |
| 4,723,549 A | 2/1988 | Wholey et al. |
| 4,727,873 A | 3/1988 | Mobin-Uddin |
| 4,732,152 A | 3/1988 | Wallsten et al. |
| 4,817,600 A | 4/1989 | Herms et al. |
| 4,824,435 A | 4/1989 | Giesy et al. |
| 4,832,055 A | 5/1989 | Palestrant |
| 4,846,794 A | 7/1989 | Hertzer |
| 4,848,343 A | 7/1989 | Wallsten et al. |
| 4,873,978 A | 10/1989 | Ginsburg |
| 4,943,297 A | 7/1990 | Saveliev et al. |
| 4,957,501 A | 9/1990 | Lahille et al. |
| 4,990,156 A | 2/1991 | Lefebvre |
| 4,998,916 A | 3/1991 | Hammerslag et al. |
| 5,053,008 A | 10/1991 | Bajaj |
| 5,059,205 A | 10/1991 | El-Nounou et al. |
| 5,069,226 A | 12/1991 | Yamauchi et al. |
| 5,078,726 A | 1/1992 | Kreamer |
| 5,100,423 A | 3/1992 | Fearnot |
| 5,108,418 A | 4/1992 | Lefebvre |
| 5,108,419 A | 4/1992 | Reger et al. |
| 5,112,347 A | 5/1992 | Taheri |
| 5,129,890 A | 7/1992 | Bates et al. |
| 5,133,733 A | 7/1992 | Rasmussen et al. |
| 5,147,379 A | 9/1992 | Sabbaghian et al. |
| 5,152,777 A | 10/1992 | Goldberg |
| 5,160,342 A | 11/1992 | Reger |
| 5,163,927 A | 11/1992 | Woker et al. |
| 5,203,772 A | 4/1993 | Hammerslag et al. |
| 5,234,458 A | 8/1993 | Metais |
| 5,242,462 A | 9/1993 | El-Nounou |
| 5,243,996 A | 9/1993 | Hall |
| 5,251,640 A | 10/1993 | Osborne |
| 5,263,964 A | 11/1993 | Purdy |
| 5,300,086 A | 4/1994 | Gory et al. |
| 5,324,304 A | 6/1994 | Rasmussen |
| 5,329,942 A | 7/1994 | Gunther et al. |
| 5,344,427 A | 9/1994 | Cottenceau et al. |
| 5,350,397 A | 9/1994 | Palermo et al. |
| 5,350,398 A | 9/1994 | Pavcnik et al. |
| 5,364,345 A | 11/1994 | Lowery et al. |
| 5,370,657 A | 12/1994 | Irie |
| 5,375,612 A | 12/1994 | Cottenceau et al. |
| 5,383,887 A | 1/1995 | Nadal |
| 5,413,586 A | 5/1995 | Dibie et al. |
| 5,415,630 A | 5/1995 | Gory et al. |
| 5,417,708 A | 5/1995 | Hall et al. |
| 5,451,233 A | 9/1995 | Yock |
| 5,458,573 A | 10/1995 | Summers |
| 5,522,881 A | 6/1996 | Lentz |
| 5,527,338 A | 6/1996 | Purdy |
| 5,531,788 A | 7/1996 | Dibie et al. |
| 5,549,551 A | 8/1996 | Peacock et al. |
| 5,549,626 A | 8/1996 | Miller et al. |
| 5,556,414 A | 9/1996 | Turi |
| 5,562,698 A | 10/1996 | Parker |
| 5,571,135 A | 11/1996 | Fraser et al. |
| 5,591,195 A | 1/1997 | Taheri et al. |
| 5,601,595 A | 2/1997 | Smith |
| 5,624,461 A | 4/1997 | Mariant |
| 5,626,605 A | 5/1997 | Irie et al. |
| 5,630,797 A | 5/1997 | Diedrich et al. |
| 5,634,942 A | 6/1997 | Chevillon et al. |
| 5,649,953 A | 7/1997 | Lefebvre |
| 5,662,703 A | 9/1997 | Yurek et al. |
| 5,669,933 A | 9/1997 | Simon et al. |
| 5,681,347 A | 10/1997 | Cathcart et al. |
| 5,690,642 A | 11/1997 | Osborne et al. |
| 5,690,667 A | 11/1997 | Gia |
| 5,693,067 A | 12/1997 | Purdy |
| 5,693,087 A | 12/1997 | Parodi |
| 5,695,518 A | 12/1997 | Laerum |
| 5,695,519 A | 12/1997 | Summers et al. |
| 5,700,253 A | 12/1997 | Parker |
| 5,709,704 A | 1/1998 | Nott et al. |
| 5,713,853 A | 2/1998 | Clark et al. |
| 5,720,764 A | 2/1998 | Naderlinger |
| 5,725,550 A | 3/1998 | Nadal |
| 5,738,667 A | 4/1998 | Solar |
| 5,746,767 A | 5/1998 | Smith |
| 5,755,772 A | 5/1998 | Evans et al. |
| 5,755,790 A | 5/1998 | Chevillon et al. |
| 5,766,203 A | 6/1998 | Imran et al. |
| 5,769,816 A | 6/1998 | Barbut et al. |
| 5,769,871 A | 6/1998 | Mers et al. |
| 5,795,322 A | 8/1998 | Boudewijn |
| 5,800,457 A | 9/1998 | Gelbfish et al. |
| 5,800,525 A | 9/1998 | Bachinski et al. |
| 5,810,874 A | 9/1998 | Lefebvre |
| 5,814,027 A | 9/1998 | Hassett et al. |
| 5,814,064 A | 9/1998 | Daniel et al. |
| 5,820,592 A | 10/1998 | Hammerslag |
| 5,827,324 A | 10/1998 | Cassell et al. |
| 5,830,230 A | 11/1998 | Berryman et al. |
| 5,836,968 A | 11/1998 | Simon et al. |
| 5,836,969 A | 11/1998 | Kim et al. |
| 5,846,260 A | 12/1998 | Maahs |
| 5,853,420 A | 12/1998 | Chevillon et al. |
| 5,876,367 A | 3/1999 | Kaganov et al. |
| 5,893,869 A | 4/1999 | Barnhart et al. |
| 5,895,391 A | 4/1999 | Farnholtz |
| 5,895,399 A | 4/1999 | Barbut et al. |
| 5,895,410 A | 4/1999 | Forber et al. |
| 5,908,435 A | 6/1999 | Samuels |
| 5,910,154 A | 6/1999 | Tsugita et al. |
| 5,911,702 A | 6/1999 | Romley et al. |
| 5,911,704 A | 6/1999 | Humes |
| 5,911,717 A | 6/1999 | Jacobsen et al. |
| 5,911,734 A | 6/1999 | Tsugita et al. |
| 5,919,224 A | 7/1999 | Thompson et al. |
| 5,925,062 A | 7/1999 | Purdy |
| 5,925,063 A | 7/1999 | Khosravi |
| 5,928,260 A | 7/1999 | Chin et al. |
| 5,928,261 A | 7/1999 | Ruiz |
| 5,938,683 A | 8/1999 | Lefebvre |
| 5,941,896 A | 8/1999 | Kerr |
| 5,944,728 A | 8/1999 | Bates |
| 5,947,985 A | 9/1999 | Imran |
| 5,947,995 A | 9/1999 | Samuels |
| 5,948,017 A | 9/1999 | Taheri |
| 5,951,567 A | 9/1999 | Javier, Jr. et al. |
| 5,954,741 A | 9/1999 | Fox |
| 5,954,742 A | 9/1999 | Osypka |
| 5,954,745 A | 9/1999 | Gertler et al. |
| 5,968,057 A | 10/1999 | Taheri |
| 5,968,071 A | 10/1999 | Chevillon et al. |
| 5,972,019 A | 10/1999 | Engelson et al. |
| 5,976,162 A | 11/1999 | Doan et al. |
| 5,976,172 A | 11/1999 | Homsma et al. |
| 5,980,555 A | 11/1999 | Barbut et al. |
| 5,984,947 A | 11/1999 | Smith |
| 5,984,965 A | 11/1999 | Knapp et al. |
| 5,989,281 A | 11/1999 | Barbut et al. |
| 6,001,118 A | 12/1999 | Daniel et al. |
| 6,007,557 A | 12/1999 | Ambrisco et al. |
| 6,007,558 A | 12/1999 | Ravenscroft et al. |
| 6,010,522 A | 1/2000 | Barbut et al. |
| 6,013,093 A | 1/2000 | Nott et al. |
| 6,015,424 A | 1/2000 | Rosenbluth et al. |
| 6,027,520 A | 2/2000 | Tsugita et al. |
| 6,036,717 A | 3/2000 | Mers Kelly et al. |
| 6,036,720 A | 3/2000 | Abrams et al. |
| 6,042,598 A | 3/2000 | Tsugita et al. |
| 6,051,014 A | 4/2000 | Jang |
| 6,051,015 A | 4/2000 | Maahs |
| 6,053,932 A * | 4/2000 | Daniel et al. .................. 606/200 |
| 6,059,745 A | 5/2000 | Gelbfish |
| 6,059,813 A | 5/2000 | Vrba et al. |
| 6,059,814 A | 5/2000 | Ladd |
| 6,063,113 A | 5/2000 | Kavteladze et al. |
| 6,066,158 A | 5/2000 | Engelson et al. |
| 6,068,645 A | 5/2000 | Tu |

| Patent | Type | Date | Inventor | Patent | Type | Date | Inventor |
|---|---|---|---|---|---|---|---|
| 6,074,357 | A | 6/2000 | Kaganov et al. | 6,312,444 | B1 | 11/2001 | Barbut |
| 6,077,274 | A | 6/2000 | Ouchi et al. | 6,319,268 | B1 | 11/2001 | Ambrisco et al. |
| 6,080,178 | A | 6/2000 | Meglin | 6,325,815 | B1 | 12/2001 | Kusleika et al. |
| 6,083,239 | A | 7/2000 | Addis | 6,325,816 | B1 | 12/2001 | Fulton, III et al. |
| 6,086,577 | A | 7/2000 | Ken et al. | 6,328,755 | B1 | 12/2001 | Marshall |
| 6,086,605 | A | 7/2000 | Barbut et al. | 6,331,183 | B1 | 12/2001 | Suon |
| 6,093,199 | A | 7/2000 | Brown et al. | 6,331,184 | B1 | 12/2001 | Abrams |
| 6,096,053 | A | 8/2000 | Bates | 6,334,864 | B1 | 1/2002 | Amplatz et al. |
| 6,096,070 | A | 8/2000 | Ragheb et al. | 6,336,934 | B1 | 1/2002 | Gilson et al. |
| 6,099,549 | A | 8/2000 | Bosma et al. | 6,338,739 | B1 | 1/2002 | Datta et al. |
| 6,106,497 | A | 8/2000 | Wang | 6,340,364 | B2 | 1/2002 | Kanesaka |
| 6,126,672 | A | 10/2000 | Berryman et al. | 6,342,062 | B1 | 1/2002 | Suon et al. |
| 6,126,673 | A | 10/2000 | Kim et al. | 6,342,063 | B1 | 1/2002 | DeVries et al. |
| 6,129,739 | A | 10/2000 | Khosravi | 6,344,048 | B1 | 2/2002 | Chin et al. |
| 6,136,016 | A | 10/2000 | Barbut et al. | 6,344,049 | B1 | 2/2002 | Levinson et al. |
| 6,146,396 | A | 11/2000 | Konya et al. | 6,346,116 | B1 | 2/2002 | Brooks et al. |
| 6,146,404 | A | 11/2000 | Kim et al. | 6,348,041 | B1 | 2/2002 | Klint |
| 6,152,931 | A | 11/2000 | Nadal et al. | 6,348,063 | B1 | 2/2002 | Yassour et al. |
| 6,152,946 | A | 11/2000 | Broome et al. | 6,350,271 | B1 | 2/2002 | Kurz et al. |
| 6,152,947 | A | 11/2000 | Ambrisco et al. | 6,355,051 | B1 | 3/2002 | Sisskind et al. |
| 6,156,061 | A | 12/2000 | Wallace et al. | 6,358,228 | B1 | 3/2002 | Tubman et al. |
| 6,156,062 | A | 12/2000 | McGuinness | 6,361,545 | B1 | 3/2002 | Macoviak et al. |
| 6,159,230 | A | 12/2000 | Samuels | 6,361,546 | B1 | 3/2002 | Khosravi |
| 6,165,179 | A | 12/2000 | Cathcart et al. | 6,361,547 | B1 | 3/2002 | Hieshima |
| 6,165,198 | A | 12/2000 | McGurk et al. | 6,364,895 | B1 | 4/2002 | Greenhalgh |
| 6,165,199 | A | 12/2000 | Barbut | 6,364,896 | B1 | 4/2002 | Addis |
| 6,165,200 | A | 12/2000 | Tsugita et al. | 6,368,338 | B1 | 4/2002 | Konya et al. |
| 6,168,579 | B1 | 1/2001 | Tsugita et al. | 6,371,961 | B1 | 4/2002 | Osborne et al. |
| 6,168,603 | B1 | 1/2001 | Leslie et al. | 6,371,969 | B1 | 4/2002 | Tsugita et al. |
| 6,168,610 | B1 | 1/2001 | Marin et al. | 6,371,970 | B1 | 4/2002 | Khosravi et al. |
| 6,168,622 | B1 | 1/2001 | Mazzocchi | 6,371,971 | B1 | 4/2002 | Tsugita et al. |
| 6,171,327 | B1 | 1/2001 | Daniel et al. | 6,375,670 | B1 | 4/2002 | Greenhalgh |
| 6,171,328 | B1 | 1/2001 | Addis | 6,379,374 | B1 | 4/2002 | Hieshima et al. |
| 6,174,318 | B1 | 1/2001 | Bates et al. | 6,380,457 | B1 | 4/2002 | Yurek et al. |
| 6,179,851 | B1 | 1/2001 | Barbut et al. | 6,383,146 | B1 | 5/2002 | Klint |
| 6,179,859 | B1 | 1/2001 | Bates et al. | 6,383,171 | B1 | 5/2002 | Gifford et al. |
| 6,179,860 | B1 | 1/2001 | Fulton, III et al. | 6,383,174 | B1 | 5/2002 | Eder |
| 6,179,861 | B1 | 1/2001 | Khosravi et al. | 6,383,193 | B1 | 5/2002 | Cathcart et al. |
| 6,187,025 | B1 | 2/2001 | Machek | 6,383,196 | B1 | 5/2002 | Leslie et al. |
| 6,193,739 | B1 | 2/2001 | Chevillon et al. | 6,383,205 | B1 | 5/2002 | Samson et al. |
| 6,203,561 | B1 | 3/2001 | Ramee et al. | 6,383,206 | B1 | 5/2002 | Gillick et al. |
| 6,206,931 | B1 | 3/2001 | Cook et al. | 6,391,044 | B1 | 5/2002 | Yadav et al. |
| 6,214,025 | B1 | 4/2001 | Thistle et al. | 6,391,045 | B1 | 5/2002 | Kim et al. |
| 6,214,026 | B1 | 4/2001 | Lepak et al. | 6,391,052 | B2 | 5/2002 | Buirge et al. |
| 6,221,091 | B1 | 4/2001 | Khosravi | 6,395,014 | B1 | 5/2002 | Macoviak et al. |
| 6,224,620 | B1 | 5/2001 | Maahs | 6,402,771 | B1 | 6/2002 | Palmer et al. |
| 6,231,588 | B1 | 5/2001 | Zadno-Azizi | 6,402,772 | B1 | 6/2002 | Amplatz et al. |
| 6,231,589 | B1 | 5/2001 | Wessman et al. | 6,409,742 | B1 | 6/2002 | Fulton, III et al. |
| 6,235,044 | B1 | 5/2001 | Root et al. | 6,413,235 | B1 | 7/2002 | Parodi |
| 6,235,045 | B1 | 5/2001 | Barbut et al. | 6,416,530 | B2 | 7/2002 | DeVries et al. |
| 6,238,412 | B1 | 5/2001 | Dubrul et al. | 6,419,686 | B1 | 7/2002 | McLeod et al. |
| 6,241,746 | B1 | 6/2001 | Bosma et al. | 6,423,052 | B1 | 7/2002 | Escano |
| 6,245,012 | B1 | 6/2001 | Kleshinski | 6,423,086 | B1 | 7/2002 | Barbut et al. |
| 6,245,087 | B1 | 6/2001 | Addis | 6,425,909 | B1 * | 7/2002 | Dieck et al. ................... 606/200 |
| 6,245,088 | B1 | 6/2001 | Lowery | 6,428,557 | B1 | 8/2002 | Hilaire |
| 6,245,089 | B1 | 6/2001 | Daniel et al. | 6,428,558 | B1 | 8/2002 | Jones et al. |
| 6,251,092 | B1 | 6/2001 | Qin et al. | 6,428,559 | B1 | 8/2002 | Johnson |
| 6,251,122 | B1 | 6/2001 | Tsukernik | 6,432,122 | B1 | 8/2002 | Gilson et al. |
| 6,254,550 | B1 | 7/2001 | McNamara et al. | 6,436,112 | B2 | 8/2002 | Wensel et al. |
| 6,254,633 | B1 | 7/2001 | Pinchuk et al. | 6,436,120 | B1 | 8/2002 | Meglin |
| 6,258,026 | B1 | 7/2001 | Ravenscroft et al. | 6,436,121 | B1 | 8/2002 | Blom |
| 6,258,115 | B1 | 7/2001 | Dubrul | 6,443,926 | B1 | 9/2002 | Kletschka |
| 6,258,120 | B1 | 7/2001 | McKenzie et al. | 6,443,971 | B1 | 9/2002 | Boylan et al. |
| 6,261,305 | B1 | 7/2001 | Marotta et al. | 6,443,972 | B1 | 9/2002 | Bosma et al. |
| 6,264,672 | B1 | 7/2001 | Fisher | 6,443,979 | B1 | 9/2002 | Stalker et al. |
| 6,267,776 | B1 | 7/2001 | O'Connell | 6,447,530 | B1 | 9/2002 | Ostrovsky et al. |
| 6,267,777 | B1 | 7/2001 | Bosma et al. | 6,447,531 | B1 | 9/2002 | Amplatz |
| 6,273,900 | B1 | 8/2001 | Nott et al. | 6,454,775 | B1 | 9/2002 | Demarais et al. |
| 6,273,901 | B1 | 8/2001 | Whitcher et al. | 6,458,139 | B1 | 10/2002 | Palmer et al. |
| 6,277,125 | B1 | 8/2001 | Barry et al. | 6,458,145 | B1 | 10/2002 | Ravenscroft et al. |
| 6,277,126 | B1 | 8/2001 | Barry et al. | 6,461,370 | B1 | 10/2002 | Gray et al. |
| 6,277,138 | B1 | 8/2001 | Levinson et al. | 6,468,290 | B1 | 10/2002 | Weldon et al. |
| 6,277,139 | B1 | 8/2001 | Levinson et al. | 6,468,291 | B2 | 10/2002 | Bates et al. |
| 6,280,451 | B1 | 8/2001 | Bates et al. | 6,482,222 | B1 | 11/2002 | Bruckheimer et al. |
| 6,287,321 | B1 | 9/2001 | Jang | 6,485,456 | B1 | 11/2002 | Kletschka |
| 6,290,710 | B1 | 9/2001 | Cryer et al. | 6,485,500 | B1 | 11/2002 | Kokish et al. |
| 6,299,604 | B1 | 10/2001 | Ragheb et al. | 6,485,501 | B1 | 11/2002 | Green |
| 6,306,163 | B1 | 10/2001 | Fitz | 6,485,502 | B2 | 11/2002 | Don Michael et al. |
| 6,309,399 | B1 | 10/2001 | Barbut et al. | 6,491,712 | B1 | 12/2002 | O'Connor |

| Patent | Date | Name |
|---|---|---|
| 6,494,895 B2 | 12/2002 | Addis |
| 6,497,709 B1 | 12/2002 | Heath |
| 6,499,487 B1 | 12/2002 | McKenzie et al. |
| 6,500,166 B1 | 12/2002 | Zadno Azizi et al. |
| 6,500,191 B2 | 12/2002 | Addis |
| 6,502,606 B2 | 1/2003 | Klint |
| 6,506,203 B1 | 1/2003 | Boyle et al. |
| 6,506,205 B2 | 1/2003 | Goldberg et al. |
| 6,508,826 B2 | 1/2003 | Murphy et al. |
| 6,511,492 B1 | 1/2003 | Rosenbluth et al. |
| 6,511,496 B1 | 1/2003 | Huter et al. |
| 6,511,497 B1 | 1/2003 | Braun et al. |
| 6,511,503 B1 | 1/2003 | Burkett et al. |
| 6,514,273 B1 | 2/2003 | Voss et al. |
| 6,517,559 B1 | 2/2003 | O'Connell |
| 6,520,978 B1 | 2/2003 | Blackledge et al. |
| 6,520,983 B1 | 2/2003 | Colgan et al. |
| 6,527,746 B1 | 3/2003 | Oslund et al. |
| 6,527,791 B2 | 3/2003 | Fisher |
| 6,527,962 B1 | 3/2003 | Nadal |
| 6,530,935 B2 | 3/2003 | Wensel et al. |
| 6,530,939 B1 | 3/2003 | Hopkins et al. |
| 6,530,940 B2 | 3/2003 | Fisher |
| 6,533,770 B1 | 3/2003 | Lepulu et al. |
| 6,533,800 B1 | 3/2003 | Barbut |
| 6,537,293 B1 | 3/2003 | Berryman et al. |
| 6,537,294 B1 | 3/2003 | Boyle et al. |
| 6,537,296 B2 | 3/2003 | Levinson et al. |
| 6,537,297 B2 | 3/2003 | Tsugita et al. |
| 6,540,722 B1 | 4/2003 | Boyle et al. |
| 6,540,767 B1 | 4/2003 | Walak et al. |
| 6,540,768 B1 | 4/2003 | Diaz et al. |
| 6,544,221 B1 | 4/2003 | Kokish et al. |
| 6,544,276 B1 | 4/2003 | Azizi |
| 6,544,278 B1 | 4/2003 | Vrba et al. |
| 6,544,279 B1 | 4/2003 | Hopkins et al. |
| 6,544,280 B1 | 4/2003 | Daniel et al. |
| 6,547,759 B1 | 4/2003 | Fisher |
| 6,551,303 B1 | 4/2003 | Van Tassel et al. |
| 6,551,341 B2 | 4/2003 | Boylan et al. |
| 6,551,342 B1 | 4/2003 | Shen et al. |
| 6,554,849 B1 | 4/2003 | Jones et al. |
| 6,558,404 B2 | 5/2003 | Tsukernik |
| 6,558,405 B1 | 5/2003 | McInnes |
| 6,558,406 B2 | 5/2003 | Okada |
| 6,562,058 B2 | 5/2003 | Seguin et al. |
| 6,565,591 B2 | 5/2003 | Brady et al. |
| 6,569,147 B1 | 5/2003 | Evans et al. |
| 6,569,183 B1 | 5/2003 | Kim et al. |
| 6,569,184 B2 | 5/2003 | Huter |
| 6,575,995 B1 | 6/2003 | Huter et al. |
| 6,575,996 B1 | 6/2003 | Denison et al. |
| 6,575,997 B1 | 6/2003 | Palmer et al. |
| 6,579,303 B2 | 6/2003 | Amplatz |
| 6,582,396 B1 | 6/2003 | Parodi |
| 6,582,447 B1 | 6/2003 | Patel et al. |
| 6,582,448 B1 | 6/2003 | Boyle et al. |
| 6,589,227 B2 | 7/2003 | Sønderskov Klint |
| 6,589,230 B2 | 7/2003 | Gia et al. |
| 6,589,263 B1 | 7/2003 | Hopkins et al. |
| 6,589,264 B1 | 7/2003 | Barbut et al. |
| 6,589,265 B1 | 7/2003 | Palmer et al. |
| 6,589,266 B2 | 7/2003 | Whitcher et al. |
| 6,592,546 B1 | 7/2003 | Barbut et al. |
| 6,592,606 B2 | 7/2003 | Huter et al. |
| 6,592,616 B1 | 7/2003 | Stack et al. |
| 6,595,983 B2 | 7/2003 | Voda |
| 6,596,011 B2 | 7/2003 | Johnson et al. |
| 6,599,275 B1 | 7/2003 | Fischer, Jr. |
| 6,599,307 B1 | 7/2003 | Huter et al. |
| 6,599,308 B2 | 7/2003 | Amplatz |
| 6,602,271 B2 | 8/2003 | Adams et al. |
| 6,602,273 B2 | 8/2003 | Marshall |
| 6,602,280 B2 | 8/2003 | Chobotov |
| 6,605,102 B1 | 8/2003 | Mazzocchi et al. |
| 6,607,506 B2 | 8/2003 | Kletschka |
| 6,610,077 B1 | 8/2003 | Hancock et al. |
| 6,611,720 B2 | 8/2003 | Hata et al. |
| 6,613,074 B1 | 9/2003 | Mitelberg et al. |
| 6,616,679 B1 | 9/2003 | Khosravi et al. |
| 6,616,680 B1 | 9/2003 | Thielen |
| 6,616,681 B2 | 9/2003 | Hanson et al. |
| 6,616,682 B2 | 9/2003 | Joergensen et al. |
| 6,620,148 B1 | 9/2003 | Tsugita |
| 6,620,182 B1 | 9/2003 | Khosravi et al. |
| 6,623,450 B1 | 9/2003 | Dutta |
| 6,623,506 B2 | 9/2003 | McGuckin, Jr. et al. |
| 6,629,953 B1 | 10/2003 | Boyd |
| 6,635,068 B1 | 10/2003 | Dubrul et al. |
| 6,635,069 B1 | 10/2003 | Teoh et al. |
| 6,635,070 B2 | 10/2003 | Leeflang et al. |
| 6,638,293 B1 | 10/2003 | Makower et al. |
| 6,638,294 B1 | 10/2003 | Palmer |
| 6,638,372 B1 | 10/2003 | Abrams et al. |
| 6,641,590 B1 | 11/2003 | Palmer et al. |
| 6,641,605 B1 | 11/2003 | Stergiopulos |
| 6,645,160 B1 | 11/2003 | Heesch |
| 6,645,220 B1 | 11/2003 | Huter et al. |
| 6,645,221 B1 | 11/2003 | Richter |
| 6,645,222 B1 | 11/2003 | Parodi et al. |
| 6,645,223 B2 | 11/2003 | Boyle et al. |
| 6,645,224 B2 | 11/2003 | Gilson et al. |
| 6,652,554 B1 | 11/2003 | Wholey et al. |
| 6,652,557 B1 | 11/2003 | MacDonald |
| 6,652,558 B2 | 11/2003 | Patel et al. |
| 6,656,201 B2 | 12/2003 | Ferrera et al. |
| 6,656,202 B2 | 12/2003 | Papp et al. |
| 6,656,203 B2 | 12/2003 | Roth et al. |
| 6,656,204 B2 | 12/2003 | Ambrisco et al. |
| 6,656,351 B2 | 12/2003 | Boyle |
| 6,660,021 B1 | 12/2003 | Palmer et al. |
| 6,663,613 B1 | 12/2003 | Evans et al. |
| 6,663,650 B2 | 12/2003 | Sepetka et al. |
| 6,663,651 B2 | 12/2003 | Krolik et al. |
| 6,663,652 B2 | 12/2003 | Daniel et al. |
| 6,676,682 B1 | 1/2004 | Tsugita et al. |
| 6,679,902 B1 | 1/2004 | Boyle et al. |
| 6,689,144 B2 | 2/2004 | Gerberding |
| 6,695,813 B1 | 2/2004 | Boyle et al. |
| 6,695,865 B2 | 2/2004 | Boyle et al. |
| 6,702,834 B1 | 3/2004 | Boylan et al. |
| 6,709,450 B2 | 3/2004 | Kang et al. |
| 6,712,835 B2 | 3/2004 | Mazzocchi et al. |
| 6,716,207 B2 | 4/2004 | Farnholtz |
| 6,716,231 B1 | 4/2004 | Rafiee et al. |
| 6,726,701 B2 | 4/2004 | Gilson et al. |
| 6,730,064 B2 | 5/2004 | Ragheb et al. |
| 6,755,855 B2 | 6/2004 | Yurek et al. |
| 6,755,856 B2 | 6/2004 | Fierens et al. |
| 6,758,855 B2 | 7/2004 | Fulton, III et al. |
| 6,761,727 B1 | 7/2004 | Ladd |
| 6,773,446 B1 | 8/2004 | Dwyer et al. |
| 6,773,448 B2 | 8/2004 | Kusleika et al. |
| 6,774,278 B1 | 8/2004 | Ragheb et al. |
| 6,780,175 B1 | 8/2004 | Sachdeva et al. |
| 6,793,667 B2 | 9/2004 | Hebert et al. |
| 6,793,668 B1 | 9/2004 | Fisher |
| 6,833,002 B2 | 12/2004 | Stack et al. |
| 6,855,154 B2 | 2/2005 | Abdel-Gawwad |
| 6,866,677 B2 | 3/2005 | Douk et al. |
| 6,866,680 B2 | 3/2005 | Yassour et al. |
| 6,872,211 B2 | 3/2005 | White et al. |
| 6,878,153 B2 | 4/2005 | Linder et al. |
| 6,896,691 B2 | 5/2005 | Boylan et al. |
| 6,929,709 B2 | 8/2005 | Smith |
| 6,932,831 B2 | 8/2005 | Forber |
| 6,936,059 B2 | 8/2005 | Belef |
| 6,939,361 B1 | 9/2005 | Kleshinski |
| 6,942,682 B2 | 9/2005 | Vrba et al. |
| 6,955,685 B2 | 10/2005 | Escamilla et al. |
| 6,964,670 B1 | 11/2005 | Shah et al. |
| 6,964,674 B1 | 11/2005 | Matsuura et al. |
| 6,969,396 B2 | 11/2005 | Krolik et al. |
| 6,974,469 B2 | 12/2005 | Broome et al. |
| 6,974,473 B2 | 12/2005 | Barclay et al. |
| 6,986,784 B1 | 1/2006 | Weiser et al. |
| 6,991,641 B2 | 1/2006 | Diaz et al. |
| 7,128,073 B1 | 10/2006 | Van Der Burg et al. |

| | | |
|---|---|---|
| 7,166,120 B2 | 1/2007 | Kusleika |
| 7,174,636 B2 | 2/2007 | Lowe |
| 7,189,249 B2 | 3/2007 | Hart et al. |
| 7,220,271 B2 | 5/2007 | Clubb et al. |
| 7,255,687 B2 | 8/2007 | Huang et al. |
| 7,285,130 B2 | 10/2007 | Austin |
| 7,306,619 B1 | 12/2007 | Palmer |
| 7,371,248 B2 | 5/2008 | Dapolito et al. |
| 7,393,358 B2 | 7/2008 | Malewicz |
| 7,604,649 B2 | 10/2009 | McGuckin et al. |
| 7,666,216 B2 | 2/2010 | Hogendijk et al. |
| 7,731,722 B2 | 6/2010 | Lavelle et al. |
| 7,766,934 B2 | 8/2010 | Pal et al. |
| 2001/0000799 A1 | 5/2001 | Wessman et al. |
| 2001/0001817 A1 | 5/2001 | Humes |
| 2001/0005789 A1 | 6/2001 | Root et al. |
| 2001/0007947 A1 | 7/2001 | Kanesaka |
| 2001/0011181 A1 | 8/2001 | DiMatteo |
| 2001/0011182 A1 | 8/2001 | Dubrul et al. |
| 2001/0012951 A1 | 8/2001 | Bates et al. |
| 2001/0016755 A1 | 8/2001 | Addis |
| 2001/0020175 A1 | 9/2001 | Yassour et al. |
| 2001/0023358 A1 | 9/2001 | Tsukernik |
| 2001/0025187 A1 | 9/2001 | Okada |
| 2001/0031980 A1 | 10/2001 | Wensel et al. |
| 2001/0031981 A1 | 10/2001 | Evans et al. |
| 2001/0031982 A1 | 10/2001 | Peterson et al. |
| 2001/0039431 A1 | 11/2001 | DeVries et al. |
| 2001/0039432 A1 | 11/2001 | Whitcher et al. |
| 2001/0041908 A1 | 11/2001 | Levinson et al. |
| 2001/0041909 A1 | 11/2001 | Tsugita et al. |
| 2001/0041928 A1 | 11/2001 | Pavcnik et al. |
| 2001/0044632 A1* | 11/2001 | Daniel et al. ............ 606/200 |
| 2001/0044634 A1 | 11/2001 | Don Michael et al. |
| 2001/0053921 A1* | 12/2001 | Jang ........................ 606/200 |
| 2002/0002383 A1 | 1/2002 | Sepetka et al. |
| 2002/0002384 A1 | 1/2002 | Gilson et al. |
| 2002/0004667 A1 | 1/2002 | Adams et al. |
| 2002/0016564 A1 | 2/2002 | Courtney et al. |
| 2002/0016609 A1 | 2/2002 | Wensel et al. |
| 2002/0022858 A1 | 2/2002 | Demond et al. |
| 2002/0022859 A1 | 2/2002 | Hogendijk |
| 2002/0026211 A1 | 2/2002 | Khosravi et al. |
| 2002/0026212 A1 | 2/2002 | Wholey et al. |
| 2002/0026213 A1 | 2/2002 | Gilson et al. |
| 2002/0032460 A1 | 3/2002 | Kusleika et al. |
| 2002/0032461 A1 | 3/2002 | Marshall |
| 2002/0042626 A1 | 4/2002 | Hanson et al. |
| 2002/0042627 A1 | 4/2002 | Brady et al. |
| 2002/0045915 A1 | 4/2002 | Balceta et al. |
| 2002/0045916 A1 | 4/2002 | Gray et al. |
| 2002/0045918 A1 | 4/2002 | Suon et al. |
| 2002/0049452 A1 | 4/2002 | Kurz et al. |
| 2002/0049468 A1 | 4/2002 | Streeter et al. |
| 2002/0052627 A1 | 5/2002 | Boylan et al. |
| 2002/0058904 A1 | 5/2002 | Boock et al. |
| 2002/0058911 A1 | 5/2002 | Gilson et al. |
| 2002/0058963 A1 | 5/2002 | Vale et al. |
| 2002/0058964 A1 | 5/2002 | Addis |
| 2002/0062133 A1 | 5/2002 | Gilson et al. |
| 2002/0062134 A1 | 5/2002 | Barbut et al. |
| 2002/0062135 A1* | 5/2002 | Mazzocchi et al. ......... 606/200 |
| 2002/0065507 A1 | 5/2002 | Zadno-Azizi |
| 2002/0068954 A1 | 6/2002 | Foster |
| 2002/0068955 A1 | 6/2002 | Khosravi |
| 2002/0072764 A1 | 6/2002 | Sepetka et al. |
| 2002/0072765 A1 | 6/2002 | Mazzocchi et al. |
| 2002/0077596 A1 | 6/2002 | McKenzie et al. |
| 2002/0082558 A1 | 6/2002 | Samson et al. |
| 2002/0082639 A1 | 6/2002 | Broome et al. |
| 2002/0087187 A1 | 7/2002 | Mazzocchi et al. |
| 2002/0090389 A1 | 7/2002 | Humes et al. |
| 2002/0091407 A1 | 7/2002 | Zadno-Azizi et al. |
| 2002/0091408 A1 | 7/2002 | Sutton et al. |
| 2002/0091409 A1 | 7/2002 | Sutton et al. |
| 2002/0095170 A1 | 7/2002 | Krolik et al. |
| 2002/0095171 A1 | 7/2002 | Belef |
| 2002/0095172 A1 | 7/2002 | Mazzocchi et al. |
| 2002/0095173 A1 | 7/2002 | Mazzocchi et al. |
| 2002/0095174 A1 | 7/2002 | Tsugita et al. |
| 2002/0099405 A1 | 7/2002 | Yurek et al. |
| 2002/0099407 A1* | 7/2002 | Becker et al. ............ 606/200 |
| 2002/0099435 A1 | 7/2002 | Stinson |
| 2002/0103501 A1 | 8/2002 | Diaz et al. |
| 2002/0107541 A1 | 8/2002 | Vale et al. |
| 2002/0111647 A1 | 8/2002 | Khairkhahan et al. |
| 2002/0111648 A1 | 8/2002 | Kusleika et al. |
| 2002/0111649 A1 | 8/2002 | Russo et al. |
| 2002/0116024 A1 | 8/2002 | Goldberg et al. |
| 2002/0120226 A1 | 8/2002 | Beck |
| 2002/0120286 A1 | 8/2002 | DoBrava et al. |
| 2002/0120287 A1 | 8/2002 | Huter |
| 2002/0123720 A1 | 9/2002 | Kusleika et al. |
| 2002/0123755 A1 | 9/2002 | Lowe et al. |
| 2002/0123759 A1 | 9/2002 | Amplatz |
| 2002/0123766 A1 | 9/2002 | Seguin et al. |
| 2002/0128679 A1 | 9/2002 | Turovskiy et al. |
| 2002/0128680 A1 | 9/2002 | Pavlovic |
| 2002/0128681 A1 | 9/2002 | Broome et al. |
| 2002/0133191 A1 | 9/2002 | Khosravi et al. |
| 2002/0133192 A1 | 9/2002 | Kusleika et al. |
| 2002/0138094 A1 | 9/2002 | Borillo et al. |
| 2002/0138095 A1 | 9/2002 | Mazzocchi et al. |
| 2002/0138096 A1 | 9/2002 | Hieshima |
| 2002/0138097 A1 | 9/2002 | Ostrovsky et al. |
| 2002/0143360 A1 | 10/2002 | Douk et al. |
| 2002/0143361 A1 | 10/2002 | Douk et al. |
| 2002/0143362 A1 | 10/2002 | Macoviak et al. |
| 2002/0151927 A1 | 10/2002 | Douk et al. |
| 2002/0151928 A1 | 10/2002 | Leslie et al. |
| 2002/0156520 A1 | 10/2002 | Boylan et al. |
| 2002/0161389 A1 | 10/2002 | Boyle et al. |
| 2002/0161390 A1 | 10/2002 | Mouw |
| 2002/0161391 A1 | 10/2002 | Murphy et al. |
| 2002/0161392 A1 | 10/2002 | Dubrul |
| 2002/0161393 A1 | 10/2002 | Demond et al. |
| 2002/0161394 A1 | 10/2002 | Macoviak et al. |
| 2002/0161395 A1 | 10/2002 | Douk et al. |
| 2002/0161396 A1 | 10/2002 | Jang et al. |
| 2002/0165557 A1 | 11/2002 | McAlister |
| 2002/0165573 A1 | 11/2002 | Barbut |
| 2002/0165576 A1 | 11/2002 | Boyle et al. |
| 2002/0165598 A1 | 11/2002 | Wahr et al. |
| 2002/0169472 A1 | 11/2002 | Douk et al. |
| 2002/0169474 A1 | 11/2002 | Kusleika et al. |
| 2002/0173815 A1 | 11/2002 | Hogendijk et al. |
| 2002/0173819 A1 | 11/2002 | Leeflang et al. |
| 2002/0177872 A1 | 11/2002 | Papp et al. |
| 2002/0177899 A1 | 11/2002 | Eum et al. |
| 2002/0183781 A1 | 12/2002 | Casey et al. |
| 2002/0183782 A1 | 12/2002 | Tsugita et al. |
| 2002/0183783 A1 | 12/2002 | Shadduck |
| 2002/0188313 A1 | 12/2002 | Johnson et al. |
| 2002/0188314 A1 | 12/2002 | Anderson et al. |
| 2002/0193824 A1 | 12/2002 | Boylan et al. |
| 2002/0193825 A1 | 12/2002 | McGuckin et al. |
| 2002/0193826 A1 | 12/2002 | McGuckin et al. |
| 2002/0193827 A1 | 12/2002 | McGuckin et al. |
| 2002/0193828 A1 | 12/2002 | Griffin et al. |
| 2002/0198561 A1 | 12/2002 | Amplatz |
| 2003/0004536 A1 | 1/2003 | Boylan et al. |
| 2003/0004537 A1 | 1/2003 | Boyle et al. |
| 2003/0004538 A1 | 1/2003 | Secrest et al. |
| 2003/0004539 A1 | 1/2003 | Linder et al. |
| 2003/0004540 A1 | 1/2003 | Linder et al. |
| 2003/0004541 A1 | 1/2003 | Linder et al. |
| 2003/0004542 A1 | 1/2003 | Wensel et al. |
| 2003/0009146 A1 | 1/2003 | Muni et al. |
| 2003/0009189 A1 | 1/2003 | Gilson et al. |
| 2003/0009190 A1 | 1/2003 | Kletschka et al. |
| 2003/0009191 A1 | 1/2003 | Wensel et al. |
| 2003/0014072 A1 | 1/2003 | Wensel et al. |
| 2003/0018354 A1 | 1/2003 | Roth et al. |
| 2003/0018355 A1 | 1/2003 | Goto et al. |
| 2003/0023263 A1 | 1/2003 | Krolik et al. |
| 2003/0023264 A1 | 1/2003 | Dieck et al. |
| 2003/0023265 A1 | 1/2003 | Forber |
| 2003/0032976 A1 | 2/2003 | Boucek |

| | | |
|---|---|---|
| 2003/0032977 A1 | 2/2003 | Brady |
| 2003/0040772 A1 | 2/2003 | Hyodoh et al. |
| 2003/0045897 A1 | 3/2003 | Huter et al. |
| 2003/0045898 A1 | 3/2003 | Harrison et al. |
| 2003/0050662 A1 | 3/2003 | Don Michael |
| 2003/0055452 A1 | 3/2003 | Joergensen et al. |
| 2003/0055480 A1 | 3/2003 | Fischell et al. |
| 2003/0060843 A1 | 3/2003 | Boucher |
| 2003/0060844 A1 | 3/2003 | Borillo et al. |
| 2003/0065354 A1 | 4/2003 | Boyle et al. |
| 2003/0065355 A1 | 4/2003 | Weber |
| 2003/0065356 A1 | 4/2003 | Tsugita et al. |
| 2003/0069596 A1 | 4/2003 | Eskuri |
| 2003/0073979 A1 | 4/2003 | Naimark et al. |
| 2003/0074019 A1 | 4/2003 | Gray et al. |
| 2003/0074054 A1 | 4/2003 | Duerig et al. |
| 2003/0078614 A1 | 4/2003 | Salahieh et al. |
| 2003/0083608 A1 | 5/2003 | Evans et al. |
| 2003/0083692 A1 | 5/2003 | Vrba et al. |
| 2003/0083693 A1 | 5/2003 | Daniel et al. |
| 2003/0088211 A1 | 5/2003 | Anderson et al. |
| 2003/0088266 A1 | 5/2003 | Bowlin |
| 2003/0093110 A1 | 5/2003 | Vale |
| 2003/0093112 A1 | 5/2003 | Addis |
| 2003/0097094 A1 | 5/2003 | Ouriel et al. |
| 2003/0097145 A1 | 5/2003 | Goldberg et al. |
| 2003/0100917 A1 | 5/2003 | Boyle et al. |
| 2003/0100918 A1 | 5/2003 | Duane |
| 2003/0100919 A1 | 5/2003 | Hopkins et al. |
| 2003/0105472 A1 | 6/2003 | McAlister |
| 2003/0105484 A1 | 6/2003 | Boyle et al. |
| 2003/0105486 A1 | 6/2003 | Murphy et al. |
| 2003/0109824 A1 | 6/2003 | Anderson et al. |
| 2003/0109897 A1 | 6/2003 | Walak et al. |
| 2003/0109916 A1 | 6/2003 | Don Michael |
| 2003/0114879 A1 | 6/2003 | Euteneuer et al. |
| 2003/0114880 A1 | 6/2003 | Hansen et al. |
| 2003/0120303 A1 | 6/2003 | Boyle et al. |
| 2003/0120304 A1 | 6/2003 | Kaganov et al. |
| 2003/0125764 A1 | 7/2003 | Brady et al. |
| 2003/0125765 A1 | 7/2003 | Blackledge et al. |
| 2003/0130680 A1 | 7/2003 | Russell |
| 2003/0130681 A1 | 7/2003 | Ungs |
| 2003/0130682 A1 | 7/2003 | Broome et al. |
| 2003/0130684 A1 | 7/2003 | Brady et al. |
| 2003/0130685 A1 | 7/2003 | Daniel et al. |
| 2003/0130686 A1 | 7/2003 | Daniel et al. |
| 2003/0130687 A1 | 7/2003 | Daniel et al. |
| 2003/0130688 A1 | 7/2003 | Daniel et al. |
| 2003/0135232 A1 | 7/2003 | Douk et al. |
| 2003/0135233 A1 | 7/2003 | Bates et al. |
| 2003/0139764 A1 | 7/2003 | Levinson et al. |
| 2003/0139765 A1 | 7/2003 | Patel et al. |
| 2003/0144685 A1 | 7/2003 | Boyle et al. |
| 2003/0144686 A1 | 7/2003 | Martinez et al. |
| 2003/0144687 A1 | 7/2003 | Brady et al. |
| 2003/0144688 A1 | 7/2003 | Brady et al. |
| 2003/0144689 A1 | 7/2003 | Brady et al. |
| 2003/0150821 A1 | 8/2003 | Bates et al. |
| 2003/0153935 A1 | 8/2003 | Mialhe |
| 2003/0153942 A1 | 8/2003 | Wang et al. |
| 2003/0153943 A1 | 8/2003 | Michael et al. |
| 2003/0153944 A1 | 8/2003 | Phung et al. |
| 2003/0153945 A1 | 8/2003 | Patel et al. |
| 2003/0158518 A1 | 8/2003 | Schonholz et al. |
| 2003/0158574 A1 | 8/2003 | Esch et al. |
| 2003/0158575 A1 | 8/2003 | Boylan et al. |
| 2003/0163158 A1 | 8/2003 | White |
| 2003/0163159 A1 | 8/2003 | Patel et al. |
| 2003/0167068 A1 | 9/2003 | Amplatz |
| 2003/0167069 A1 | 9/2003 | Gonzales et al. |
| 2003/0171769 A1 | 9/2003 | Barbut |
| 2003/0171770 A1 | 9/2003 | Kusleika et al. |
| 2003/0171771 A1 | 9/2003 | Anderson et al. |
| 2003/0171772 A1 | 9/2003 | Amplatz |
| 2003/0171800 A1 | 9/2003 | Bicek et al. |
| 2003/0171803 A1 | 9/2003 | Shimon |
| 2003/0176884 A1 | 9/2003 | Berrada et al. |
| 2003/0176885 A1 | 9/2003 | Broome et al. |
| 2003/0176886 A1 | 9/2003 | Wholey et al. |
| 2003/0176887 A1 | 9/2003 | Petersen |
| 2003/0176888 A1 | 9/2003 | O'Connell |
| 2003/0176889 A1 | 9/2003 | Boyle et al. |
| 2003/0181942 A1 | 9/2003 | Sutton et al. |
| 2003/0181943 A1 | 9/2003 | Daniel et al. |
| 2003/0717769 | 9/2003 | Barbut |
| 2003/0187474 A1 | 10/2003 | Keegan et al. |
| 2003/0187475 A1 | 10/2003 | Tsugita et al. |
| 2003/0187495 A1 | 10/2003 | Cully et al. |
| 2003/0191492 A1 | 10/2003 | Gellman et al. |
| 2003/0191493 A1 | 10/2003 | Epstein et al. |
| 2003/0195554 A1 | 10/2003 | Shen et al. |
| 2003/0195555 A1 | 10/2003 | Khairkhahan et al. |
| 2003/0195556 A1 | 10/2003 | Stack et al. |
| 2003/0199819 A1 | 10/2003 | Beck |
| 2003/0199917 A1 | 10/2003 | Knudson et al. |
| 2003/0199918 A1 | 10/2003 | Patel et al. |
| 2003/0199919 A1 | 10/2003 | Palmer et al. |
| 2003/0199920 A1 | 10/2003 | Boylan et al. |
| 2003/0199921 A1 | 10/2003 | Palmer et al. |
| 2003/0204168 A1 | 10/2003 | Bosma et al. |
| 2003/0204202 A1 | 10/2003 | Palmer et al. |
| 2003/0204203 A1 | 10/2003 | Khairkhahan et al. |
| 2003/0208222 A1 | 11/2003 | Zadno-Azizi |
| 2003/0208224 A1 | 11/2003 | Broome |
| 2003/0208225 A1 | 11/2003 | Goll et al. |
| 2003/0208226 A1 | 11/2003 | Bruckheimer et al. |
| 2003/0208227 A1 | 11/2003 | Thomas |
| 2003/0208228 A1 | 11/2003 | Gilson et al. |
| 2003/0208229 A1 | 11/2003 | Kletschka |
| 2003/0208253 A1 | 11/2003 | Beyer et al. |
| 2003/0212428 A1 | 11/2003 | Richter |
| 2003/0212429 A1 | 11/2003 | Keegan et al. |
| 2003/0212431 A1 | 11/2003 | Brady et al. |
| 2003/0212432 A1 | 11/2003 | Khairkhahan et al. |
| 2003/0212433 A1 | 11/2003 | Ambrisco et al. |
| 2003/0212434 A1 | 11/2003 | Thielen |
| 2003/0216774 A1 | 11/2003 | Larson |
| 2003/0220665 A1 | 11/2003 | Eskuri et al. |
| 2003/0220667 A1 | 11/2003 | Van der Burg et al. |
| 2003/0225418 A1 | 12/2003 | Esksuri et al. |
| 2003/0225435 A1 | 12/2003 | Huter et al. |
| 2003/0229374 A1 | 12/2003 | Brady et al. |
| 2003/0233117 A1 | 12/2003 | Adams et al. |
| 2004/0006364 A1 | 1/2004 | Ladd |
| 2004/0006365 A1 | 1/2004 | Brady et al. |
| 2004/0006370 A1 | 1/2004 | Tsugita |
| 2004/0015152 A1 | 1/2004 | Day |
| 2004/0039412 A1 | 2/2004 | Isshiki et al. |
| 2004/0049226 A1 | 3/2004 | Keegan et al. |
| 2004/0054394 A1 | 3/2004 | Lee |
| 2004/0054395 A1 | 3/2004 | Lee et al. |
| 2004/0059372 A1 | 3/2004 | Tsugita |
| 2004/0064067 A1 | 4/2004 | Ward |
| 2004/0064179 A1 | 4/2004 | Linder et al. |
| 2004/0068271 A1 | 4/2004 | McAlister |
| 2004/0078044 A1 | 4/2004 | Kear |
| 2004/0082962 A1 | 4/2004 | Demarais et al. |
| 2004/0088038 A1 | 5/2004 | Dehnad et al. |
| 2004/0093009 A1 | 5/2004 | Denison et al. |
| 2004/0093012 A1 | 5/2004 | Cully et al. |
| 2004/0093016 A1 | 5/2004 | Root et al. |
| 2004/0093059 A1 | 5/2004 | Lee et al. |
| 2004/0098022 A1 | 5/2004 | Barone |
| 2004/0098026 A1 | 5/2004 | Joergensen et al. |
| 2004/0098033 A1 | 5/2004 | Leeflang et al. |
| 2004/0098112 A1 | 5/2004 | DiMatteo et al. |
| 2004/0102719 A1 | 5/2004 | Keith et al. |
| 2004/0106944 A1 | 6/2004 | Daniel et al. |
| 2004/0116831 A1 | 6/2004 | Vrba |
| 2004/0133232 A1 | 7/2004 | Rosenbluth et al. |
| 2004/0138696 A1 | 7/2004 | Drasler et al. |
| 2004/0153118 A1 | 8/2004 | Clubb et al. |
| 2004/0158278 A1 | 8/2004 | Becker et al. |
| 2004/0162576 A1* | 8/2004 | Barbut et al. .............. 606/200 |
| 2004/0164030 A1 | 8/2004 | Lowe et al. |
| 2004/0167567 A1 | 8/2004 | Cano et al. |
| 2004/0176794 A1 | 9/2004 | Khosravi |

| | | |
|---|---|---|
| 2004/0176833 A1 | 9/2004 | Pavcnik et al. |
| 2004/0199203 A1 | 10/2004 | Oslund et al. |
| 2004/0204737 A1 | 10/2004 | Boismier et al. |
| 2004/0215322 A1 | 10/2004 | Kerr |
| 2004/0225321 A1 | 11/2004 | Krolik et al. |
| 2004/0236369 A1 | 11/2004 | Dubrul |
| 2005/0004663 A1 | 1/2005 | Llanos et al. |
| 2005/0021125 A1 | 1/2005 | Stack et al. |
| 2005/0027345 A1 | 2/2005 | Horan et al. |
| 2005/0038468 A1 | 2/2005 | Panetta et al. |
| 2005/0038503 A1 | 2/2005 | Greenhaigh |
| 2005/0043743 A1 | 2/2005 | Dennis |
| 2005/0043756 A1 | 2/2005 | Lavelle et al. |
| 2005/0043780 A1 | 2/2005 | Gifford et al. |
| 2005/0049668 A1 | 3/2005 | Jones et al. |
| 2005/0126979 A1 | 6/2005 | Lowe et al. |
| 2005/0137696 A1 | 6/2005 | Salahieh et al. |
| 2005/0149110 A1 | 7/2005 | Wholey et al. |
| 2005/0165480 A1 | 7/2005 | Jordan et al. |
| 2005/0177186 A1 | 8/2005 | Cully et al. |
| 2005/0177246 A1 | 8/2005 | Datta et al. |
| 2005/0197688 A1 | 9/2005 | Theron et al. |
| 2005/0209634 A1 | 9/2005 | Brady et al. |
| 2005/0216053 A1 | 9/2005 | Douk et al. |
| 2005/0217767 A1 | 10/2005 | Barvosa-Carter et al. |
| 2005/0228474 A1 | 10/2005 | Laguna |
| 2006/0009798 A1 | 1/2006 | Callister et al. |
| 2006/0009799 A1 | 1/2006 | Kleshinski et al. |
| 2006/0020334 A1 | 1/2006 | Lashinski et al. |
| 2006/0030923 A1 | 2/2006 | Gunderson |
| 2006/0074474 A1 | 4/2006 | Theron |
| 2006/0100544 A1 | 5/2006 | Ayala et al. |
| 2006/0100545 A1 | 5/2006 | Ayala et al. |
| 2006/0161241 A1 | 7/2006 | Barbut et al. |
| 2006/0184194 A1 | 8/2006 | Pal et al. |
| 2006/0200221 A1 | 9/2006 | Malewicz |
| 2006/0229660 A1 | 10/2006 | Pal et al. |
| 2006/0264707 A1 | 11/2006 | Kinney |
| 2006/0287668 A1 | 12/2006 | Fawzi et al. |
| 2007/0038241 A1 | 2/2007 | Pal |
| 2007/0100372 A1 | 5/2007 | Schaeffer |
| 2007/0112374 A1 | 5/2007 | Paul, Jr. et al. |
| 2007/0129752 A1 | 6/2007 | Webler et al. |
| 2007/0149996 A1 | 6/2007 | Coughlin |
| 2007/0167974 A1 | 7/2007 | Cully et al. |
| 2007/0185521 A1 | 8/2007 | Bui et al. |
| 2007/0250108 A1 | 10/2007 | Boyle et al. |
| 2007/0288054 A1 | 12/2007 | Tanaka et al. |
| 2008/0015518 A1 | 1/2008 | Huang et al. |
| 2008/0027481 A1 | 1/2008 | Gilson et al. |
| 2008/0103522 A1 | 5/2008 | Steingisser et al. |
| 2008/0154236 A1 | 6/2008 | Elkins et al. |
| 2008/0167629 A1 | 7/2008 | Dann et al. |
| 2008/0255587 A1 | 10/2008 | Cully et al. |
| 2008/0255606 A1 | 10/2008 | Mitra et al. |
| 2008/0262337 A1 | 10/2008 | Falwell et al. |
| 2008/0275569 A1 | 11/2008 | Lesh |

FOREIGN PATENT DOCUMENTS

| | | |
|---|---|---|
| EP | 1127556 A2 | 8/2001 |
| EP | 1310219 A2 | 5/2003 |
| EP | 1516601 | 3/2005 |
| EP | 1557137 A1 | 7/2005 |
| WO | WO 92/03097 | 3/1992 |
| WO | WO 96/10591 | 4/1996 |
| WO | WO 99/16382 | 4/1999 |
| WO | WO 99/23976 | 5/1999 |
| WO | WO 99/44510 | 9/1999 |
| WO | WO 01/82831 | 11/2001 |
| WO | WO 03/077799 A2 | 9/2003 |
| WO | WO 2006/138391 A2 | 12/2006 |

OTHER PUBLICATIONS

International Search Report and Written Opinion for PCT/US2007/020300.
Grummon, David S. et al., Appl. Phys. Lett., 82, 2727 (2003), pp. 2727.
Rubicon Embolic Filter, The Next Generation of EM, Rubicon Medical, www.rubiconmed.com, 2005.
Heeschen et al., Nature Medicine 7 (2001), No. 7, pp. 833-839.
Johnson et al., Circulation Research 94 (2004), No. 2, pp. 262-268.
International Search Report and Written Opinion for PCT/US2007/020300, 2008.
Brochure, "Shuttle Select™ System for Carotid Artery Access," (2004), pp. 1-3.
Brochure, "Slip-Cath® Angiographic Selective Catheters," (2004), pp. 1-6.
Finol, E.A. et al., "Performance Assessment of Embolic Protection Filters for Carotid Artery Stenting," *Modelling in Medicine and Biology IV*, (2005), vol. 8, pp. 133.

* cited by examiner

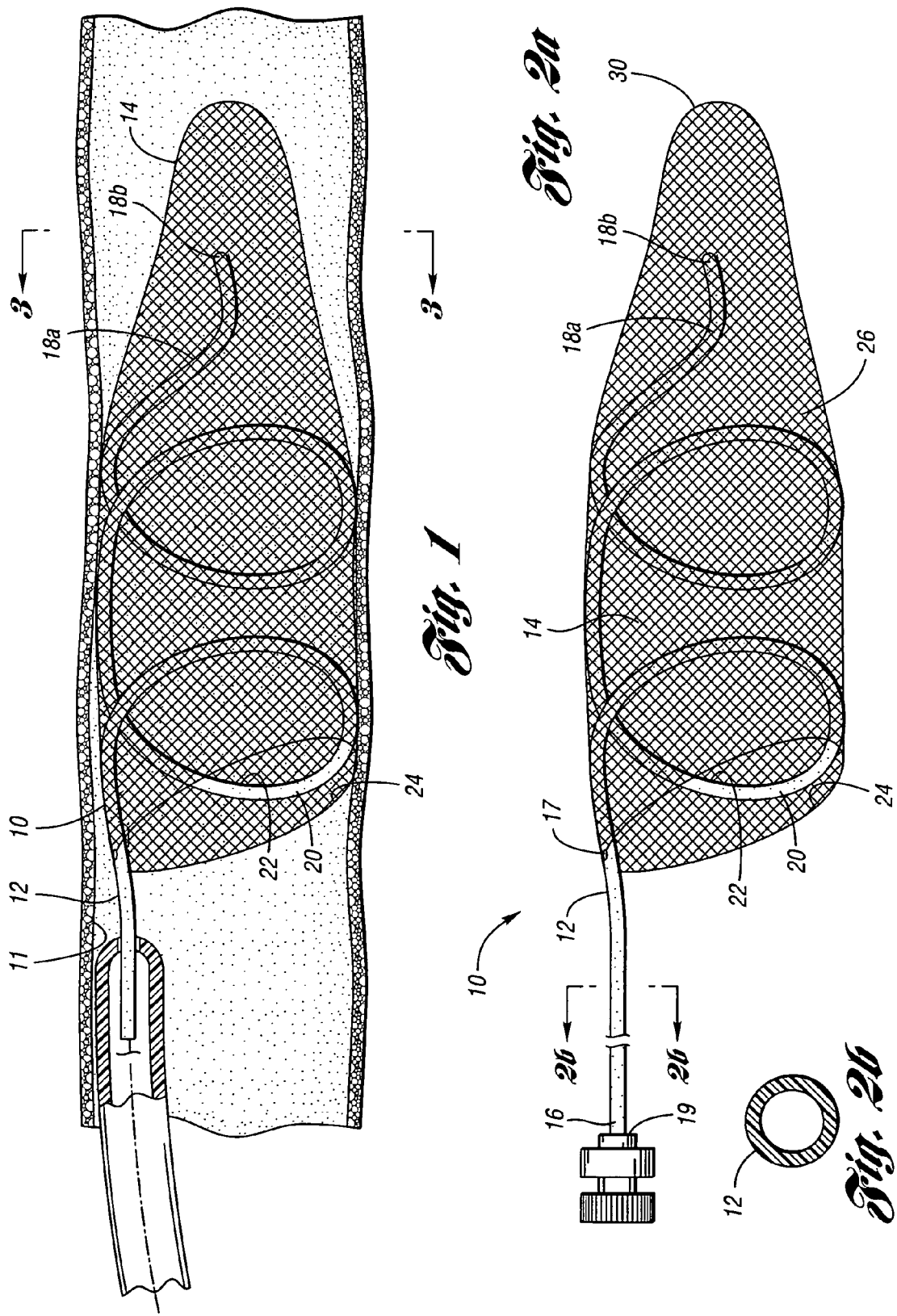

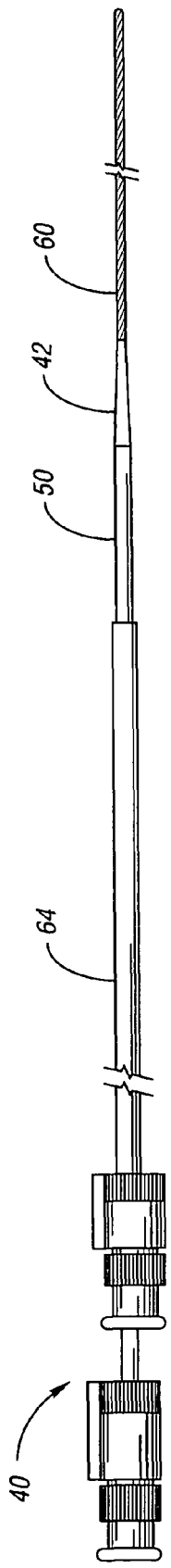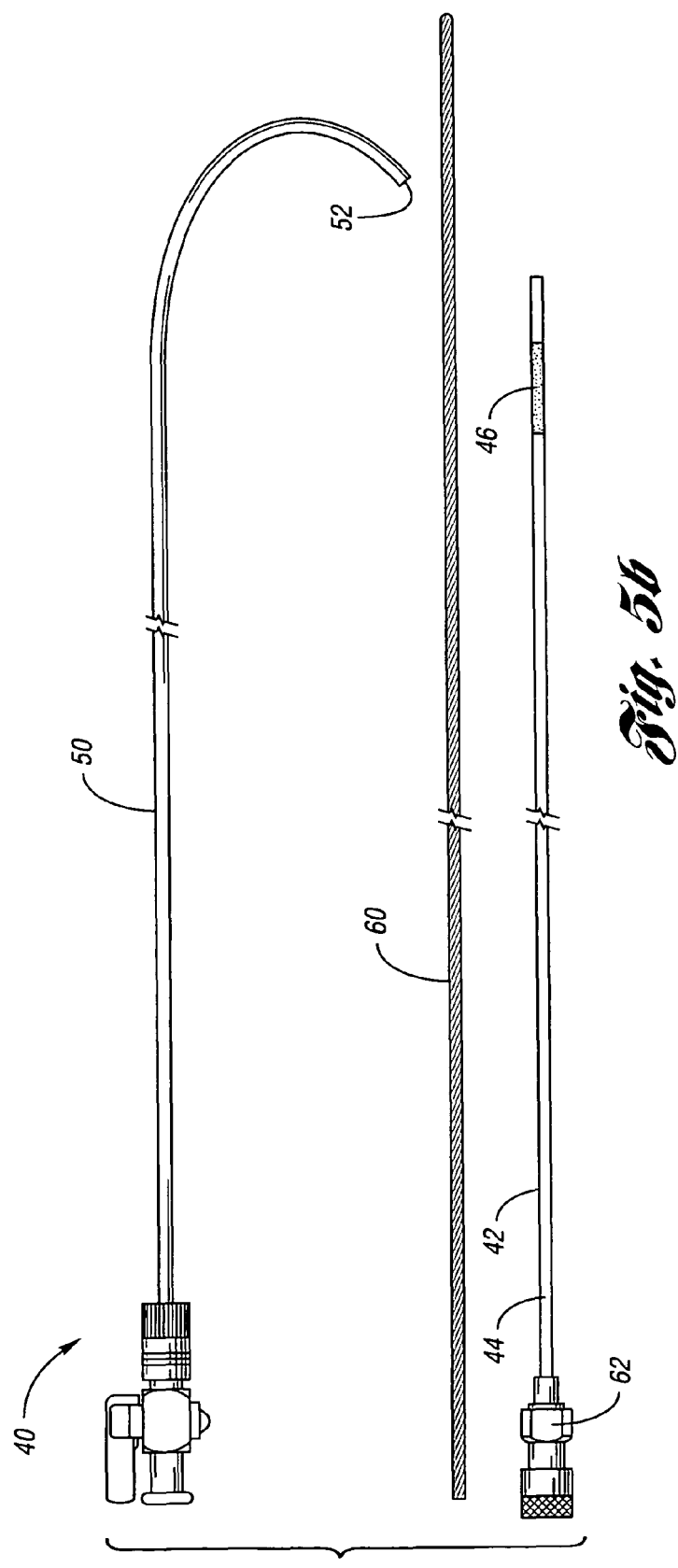
Fig. 5a
Fig. 5b

EMBOLIC PROTECTION DEVICE HAVING INFLATABLE FRAME

CROSS-REFERENCE TO RELATED APPLICATION

This patent application claims the benefit under 35 U.S.C. §119(e) of U.S. provisional patent application Ser. No. 60/705,575, filed Aug. 4, 2005 and entitled EMBOLIC PROTECTION DEVICE HAVING INFLATABLE FRAME, the entire contents of which are incorporated herein by reference.

BACKGROUND OF THE INVENTION

The present invention relates to medical devices. More particularly, the present invention relates to embolic protection devices and methods for capturing emboli within a body vessel.

Treatments for a stenotic lesion provide a potential in releasing blood clots and other thrombi plaque in the vasculature of the patient. One example is the treatment for a carotid artery stenosis. Generally, carotid artery stenosis is the narrowing of the carotid arteries, the main arteries in the neck that supply blood to the brain. Carotid artery stenosis (also called carotid artery disease) is a relatively high risk factor for ischemic stroke. The narrowing is usually caused by plaque build-up in the carotid artery. Plaque forms when cholesterol, fat and other substances form in the inner lining of an artery. This formation process is called atherosclerosis.

Depending on the degree of stenosis and the patient's overall condition, carotid artery stenosis has been treated with surgery. The procedure (with its inherent risks) is called carotid endarterectomy, which removes the plaque from the arterial walls. Carotid endarterectomy has proven to benefit patients with arteries substantially narrowed, e.g., by about 70% or more. For people with less narrowed arteries, e.g., less than about 50%, an anti-clotting drug may be prescribed to reduce the risk of ischemic stroke. Examples of these drugs are anti-platelet agents and anticoagulants.

Carotid angioplasty is a more recently developed treatment for carotid artery stenosis. This treatment uses balloons and/or stents to open a narrowed artery. Carotid angioplasty is a procedure that can be performed via a standard percutaneous transfemoral approach with the patient anesthetized using light intravenous sedation. At the stenosis area, an angioplasty balloon is delivered to predilate the stenosis in preparation for stent placement. The balloon is then removed and exchanged via catheter for a stent delivery device. Once in position, a stent is deployed across the stenotic area. If needed, an additional balloon can be placed inside the deployed stent for post-dilation to make sure the struts of the stent are pressed firmly against the inner surface of the vessel wall.

During the stenosis procedure however, there is a risk of such blood clots and thrombi being undesirably released into the blood flow within the vasculature. Embolic protection to capture emboli within the vasculature is a growing concern in the medical industry. Currently, there are a number of approaches for embolic protection to prevent emboli from traveling within the vasculature, causing an undesirable embolism, e.g., pulmonary embolism. For example, vena cava filters are more commonly being used for trapping blood clots and emboli in the vena cava filter to prevent pulmonary embolism. Also, anti-platelet agents and anticoagulants may be used to breakdown blood clots. Moreover, snares and baskets (e.g., stone retrieval baskets) are more commonly used for retrieving urinary calculi. Additionally, occlusion coils are commonly used to occlude aneurysms and accumulate thrombi in a body vessel. Embolic or distal protection devices have been implemented to capture emboli from a stenotic lesion undergoing angioplasty.

During delivery or retrieval of an embolic protection device, it is desired that the cross over profile of the device is maintained as small as possible to minimize contact with the stenotic lesion. Contact with the stenotic lesion increases the risk of blood clots and thrombi being undesirably released into the blood flow within the vasculature. Moreover, during retrieval of the embolic protection device, there is also a risk of the trapped emboli escaping therefrom. This may occur during retrieval of the device and emboli trapped therein.

Thus, there is a need to provide improved devices and methods for distally protecting and capturing emboli within a body lumen during a stenosis procedure.

BRIEF SUMMARY OF THE INVENTION

In one aspect of the present invention, an embolic protection device is provided for capturing emboli during treatment of a stenotic lesion in a body vessel. In one embodiment, the embolic protection device includes an inflatable frame having a deployed state and an undeployed state. The inflatable frame includes a distal portion having a predetermined shape and extending freely to a closed distal end when the inflatable frame is in the deployed state.

In another aspect of the present invention, an embolic protection assembly is provided for capturing emboli during treatment of a stenotic lesion in a body vessel. The assembly includes a balloon catheter having a tubular body portion and an expandable balloon fluidly connected to the tubular body, and an embolic protection device at least partially coaxially disposed within the balloon catheter during treatment of the stenotic lesion in the body vessel. The embolic protection device includes an inflatable frame having a deployed state and an undeployed state. When in the deployed state, a distal portion of the inflatable frame defines a predetermined shape and extends freely to a closed distal end.

In another aspect of the present invention, a method is provided for embolic protection during treatment of a stenotic lesion in a body vessel. The method includes percutaneously introducing a balloon catheter in the body vessel, disposing an embolic protection device coaxially within the balloon catheter such that an inflatable frame and a filter of the embolic protection device are in an undeployed state, and delivering fluid to the proximal opening of the inflatable frame. The inflatable frame and the filter are thus expanded to the deployed state such that a lip of the filter defines an open end and a distal portion of the inflatable frame defines a predetermined shape.

Further objects, features, and advantages of the present invention will become apparent from consideration of the following description and the appended claims when taken in connection with the accompanying drawings.

BRIEF DESCRIPTION OF THE DRAWINGS

FIG. 1 is an environmental view of the embolic protection device in accordance with one embodiment of the present invention;

FIG. 2a is an elevated view of the embolic protection device in FIG. 1;

FIG. 2b is a cross-sectional view of an inflatable frame of the device taken along line 2b-2b;

FIG. 3 is an end view of the embolic protection device of FIG. 2a;

FIG. 5a is a side view of an embolic protection assembly for capturing emboli during treatment of a stenotic lesion in a body vessel in accordance with one embodiment of the present invention;

FIG. 5b is an exploded view of the assembly in FIG. 5a; and

DETAILED DESCRIPTION OF THE INVENTION

Figure 3:
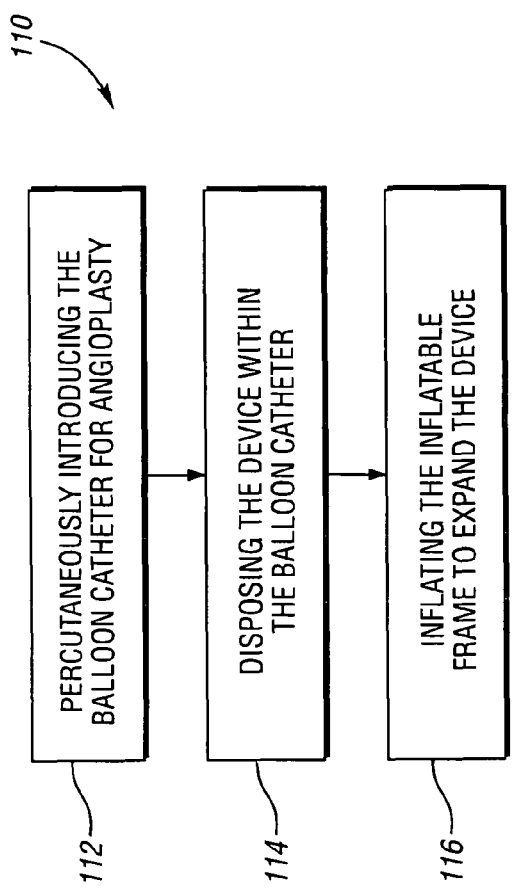

The present invention generally provides an embolic protection device for capturing emboli during treatment of a stenotic lesion in a body vessel. Embodiments of the present invention provide a device having a reduced cross-sectional profile for delivery of the device during predilitation of the stenotic lesion, and a more simple and efficient way of maintaining emboli trapped therein during retrieval of the device. In one embodiment, the device includes an inflatable frame that closes in a collapsed (or undeployed) state during delivery and retrieval of the device. In the collapsed state, the inflatable frame is deflated allowing the device to have a reduced cross-sectional profile.

FIG. 1 illustrates an embolic protection device 10 for capturing emboli during treatment of a stenotic lesion in a body vessel 11 in accordance with one embodiment of the present invention. As depicted in FIGS. 1-2b, the embolic protection device 10 comprises an inflatable frame 12 and a filter 14 attached about the inflatable frame 12. In this embodiment, the inflatable frame 12 is configured to inflate and expand in an expanded (or deployed) state and is configured to deflate and collapse in the collapsed (or undeployed) state. Preferably, the inflatable frame 12 has a proximal portion 16 extending to a distal portion 18a. As shown, the distal portion 18a has a predetermined shape in the deployed state and extends freely to a closed distal end 18b. The proximal portion 16 has a proximal opening 19 for receiving fluid therethrough. As will be described in greater detail below, the inflatable frame 12 may be in fluid communication with a proximal port for allowing fluid to enter and exit therethrough.

As shown in FIGS. 2a and 3, the distal portion 18a extends freely to the closed distal end 18b, independent of any member or mechanism connected thereto for support. This advantageously reduces the cross-sectional profile of the device 10 and a respective balloon catheter when in an undeployed state, thereby lowering the risk of undesirable pre-release of emboli during percutaneous insertion in the vasculature of a patient.

Figure 4A:
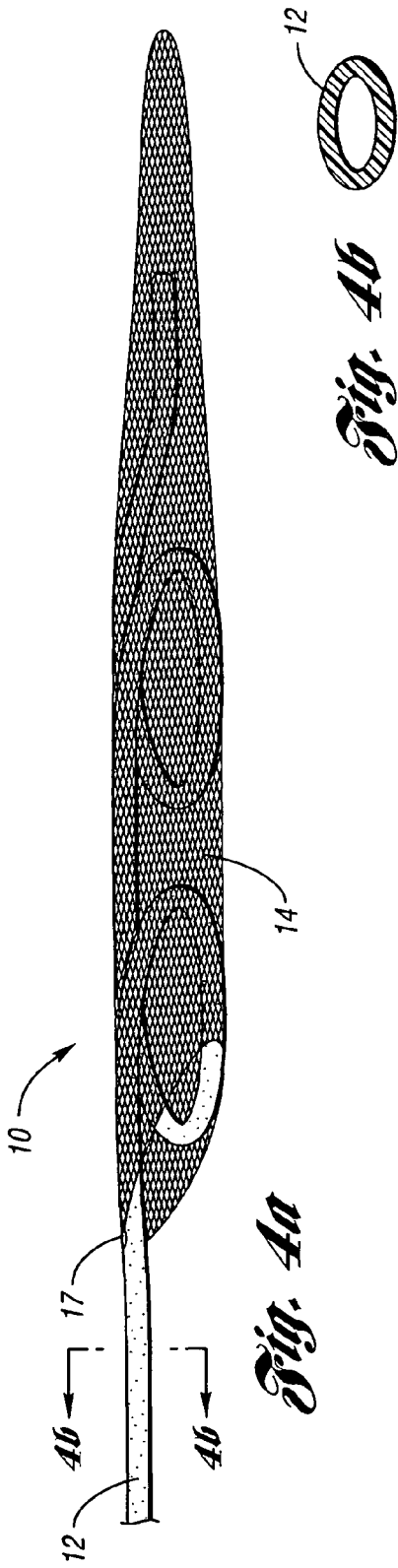
FIG. 4a is a side view of the embolic protection device in a collapsed state in accordance with one embodiment of the present invention.
Figure 4B:
FIG. 4b is a cross-sectional view of the inflatable frame of the device taken along line 4b-4b.

The inflatable frame 12 may be inflated to its deployed state (FIG. 2a) and deflated to its undeployed state (FIGS. 4a-4b) by way of a fluid such as saline. For example, saline may be flushed through the proximal opening 19 to the proximal portion 16 and the distal portion 18a. Exit of the fluid from the frame 12 defines the collapsed state of the frame 12. This advantageously further reduces the cross-over profile of the device 10 and the respective balloon catheter, lowering the risk of undesirable pre-release of emboli during percutaneous insertion in the vasculature of a patient. This is accomplished since the inflatable frame 12 is preferably comprised of shape memory material or is configured to have shape memory such that the frame 12 may be collapsed within a relatively small lumen of a catheter, e.g., balloon catheter, when in the collapsed state for potentially easier and safer delivery (and retrieval) prior to angioplasty.

The proximal opening 19 is in fluid communication with the closed distal end 18b of the inflatable frame 12 to allow for fluid to enter and exit through the proximal opening 19. In this embodiment, the proximal opening 19 is in fluid communication with a proximal port. The proximal port is attached about the inflatable frame 12 at the proximal opening 19 thereof and is configured to be in fluid communication with the closed distal end 18b. The proximal port is able to be selectively opened and closed. When in the opened position, the proximal port opens the proximal opening 19 and allows fluid to flow therethrough so that the fluid may be injected therethrough to inflate the inflatable frame 12. When in the closed position, the proximal port closes the proximal opening 19 and restricts fluid flow therethrough. Once the frame 12 is inflated with fluid, the proximal port may be closed, thereby restricting the fluid from exiting and thereby maintaining the frame 12 in the expanded state.

As mentioned above, the inflatable frame 12 may be made of shape memory material, or may be configured to have shape memory defining the predetermined shape thereof in the deployed state. For example, the inflatable frame 12 may be comprised of any suitable material such as a pre-configured polymeric material, superelastic material, stainless steel wire, cobalt-chromium-nickel-molybdenum-iron alloy, or cobalt-chrome alloy. In one example, the inflatable frame may be made of pre-configured polymeric material which takes on a predetermined shape, e.g. helical, when in the expanded state.

It is understood that the inflatable frame 12 may be formed of any other suitable material that will result in a self-opening or self-expanding device 10, such as shape memory materials or alloys. Shape memory alloys have the desirable property of becoming rigid, i.e., returning to a remembered state, when heated above a transition temperature. A shape memory alloy suitable for the present invention is Ni—Ti available under the more commonly known name Nitinol. When this material is heated above the transition temperature, the material undergoes a phase transformation from martensite to austenic, such that material returns to its remembered state. The transition temperature is dependent on the relative proportions of the alloying elements Ni and Ti and the optional inclusion of alloying additives.

In one example, the inflatable frame 12 is made from material including Nitinol with a transition temperature that is slightly below normal body temperature of humans, which is about 98.6° F. Thus, when the device 10 is deployed in a device 10 vessel and exposed to normal body temperature, the alloy of the inflatable frame 12 will transform to austenite, that is, the remembered state, which for one embodiment of the present invention is the expanded configuration when the device 10 is deployed in the body vessel. To remove the device 10, the inflatable frame 12 is cooled to transform the material to martensite which is more ductile than austenite, making the inflatable frame 12 more malleable. For example, the frame 12 may be cooled by the introduction of a cooled fluid through the proximal opening 19. Once the frame 12 is sufficiently cooled, the fluid may be withdrawn therefrom to facilitate the collapse of the device 10 and the placement of the frame within a lumen of a catheter for removal.

As shown in FIGS. 2a and 3, the predetermined shape includes at least one helical portion 20 having a helical configuration. The at least one helical portion 20 is configured to distally extend freely, independent of a support member or mechanism, to the closed distal end 18b of the inflatable frame 12. This advantageously allows the device 10 and a respective balloon catheter to have a relatively smaller crossover profile, reducing the risk of undesirable release of emboli prior to inflating the frame 12. In this embodiment, the predetermined shape includes a plurality of helical portions 20 having a helical configuration. Each of the helical portions 20 is in longitudinally overlapping relationship with the other helical portion 20. As shown, the helical portions 20 distally extend freely to the closed distal end 18b.

FIGS. 1-2b further depict a filter 14 of the embolic protection device 10 having a lip 22 attached preferably at a point 17 on the distal portion 18a and disposed freely about the frame 12, defining an open end 24 of the filter 14 when the inflatable frame 12 is in the deployed state. As shown, the filter 14 has a filter body 26 extending from the lip 22 about the inflatable frame 12 to a closed tail 30. Preferably, the filter body 26 retains the helical portions 20 of the inflatable frame 12 therein in the deployed state. The lip 22 may be attached at the point 17 on the distal portion 18 by any suitable means including sonic bonding, thermal bonding, or adhesive bonding. The filter 14 preferably extends from the lip 22 to the closed tail 30 formed to be a proximally facing concave shape. The opening of the filter 14 is configured to face toward the stenotic lesion.

The filter 14 may be comprised of or coated with any suitable material to be used for capturing emboli from the stenotic lesion during treatment thereof. In one embodiment, the filter 14 is made of connective tissue material or reconstituted or naturally-derived collagenous materials for capturing emboli. Such materials that are at least bioresorbable will provide advantage in the present invention, with materials that are bioremodelable and promote cellular invasion and ingrowth providing particular advantage.

Suitable bioremodelable materials can be provided by collagenous extracellular matrix materials (ECMs) possessing biotropic properties, including in certain forms angiogenic collagenous extracellular matrix materials. For example, suitable collagenous materials include ECMs such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa.

As prepared, the submucosa material and any other ECM used may optionally retain growth factors or other bioactive components native to the source tissue. For example, the submucosa or other ECM may include one or more growth factors such as basic fibroblast growth factor (FGF-2), transforming growth factor beta (TGF-beta), epidermal growth factor (EGF), and/or platelet derived growth factor (PDGF). As well, submucosa or other ECM used in the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein or gene expression.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multiaxial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with specific staining. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the infiltration of new blood vessels. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of native bioactive components, non-native bioactive components such as those synthetically produced by recombinant technology or other methods, may be incorporated into the submucosa or other ECM tissue. These non-native bioactive components may be naturally-derived or recombinantly produced proteins that correspond to those natively occurring in the ECM tissue, but perhaps of a different species (e.g. human proteins applied to collagenous ECMs from other animals, such as pigs). The non-native bioactive components may also be drug substances. Illustrative drug substances that may be incorporated into and/or onto the ECM materials used in the invention include, for example, antibiotics or thrombus-promoting substances such as blood clotting factors, e.g. thrombin, fibrinogen, and the like. These substances may be applied to the ECM material as a premanufactured step, immediately prior to the procedure (e.g. by soaking the material in a solution containing a suitable antibiotic such as cefazolin), or during or after engraftment of the material in the patient.

Submucosa or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of the submucosa tissue used in the present invention.

In this embodiment, SIS is used to allow the filter 14 to temporarily adhere to the walls of a body vessel in which the device 10 is deployed. SIS has a natural adherence or wettability to body fluids and connective cells comprising the connective tissue of a body vessel wall. Due to the temporary nature of the duration in which the device 10 is deployed in the body vessel, host cells of the wall will adhere to the filter 14 but not differentiate, allowing for retrieval of the device 10 from the body vessel.

In other embodiments, the filter 14 may also be made of a mesh/net cloth, nylon, biocompatible polymeric material, Teflon™, or woven mixtures thereof or any other suitable filtering material known in the art.

FIGS. 5*a* and 5*b* depict an embolic protection assembly 40 for capturing emboli during treatment of a stenotic lesion in a body vessel in accordance with another embodiment of the present invention. As shown, the assembly 40 comprises a balloon catheter 42 having a tubular body 44 and an expandable balloon 46 attached to and in fluid communication with the tubular body 44 for angioplasty at a stenotic lesion. In this embodiment, the assembly 40 comprises the embolic protection device 10 mentioned above. The tubular body 44 is preferably made of soft flexible material such as silicon or any other suitable material. In this embodiment, the balloon catheter 42 may include an outer lumen and an inner lumen. The outer lumen may be in fluid communication with the balloon for inflating and deflating the balloon. The inner lumen may be formed therethrough for percutaneous guidance through the body vessel.

As shown, the assembly 40 further includes an inner catheter 50 having a distal end 52 through which the balloon catheter 42 is disposed for deployment in the body vessel. The inner catheter 50 is preferably made of a soft, flexible material such as silicon or any other suitable material. Generally, the inner catheter 50 further has a proximal end 54 and a plastic adaptor or hub 56 to receive the embolic protection device 10 and balloon catheter 42 to be advanced therethrough. The size of the inner catheter 50 is based on the size of the body vessel in which it percutaneously inserts, and the size of the balloon catheter 42.

As shown, the assembly 40 may also include a wire guide 60 configured to be percutaneously inserted within the vasculature to guide the inner catheter 50 to a location adjacent a stenotic lesion. The wire guide 60 provides the inner catheter 50 (and balloon catheter 42) a path during insertion within the body vessel. The size of the wire guide 60 is based on the inside diameter of the inner catheter 50.

In one embodiment, the balloon catheter 42 has a proximal fluid hub 62 in fluid communication with the balloon via the outer lumen for fluid to be passed therethrough for inflation and deflation of the balloon during treatment of the stenotic lesion.

As shown, the embolic protection device 10 is coaxially disposed through the inner lumen of the balloon catheter 42 prior to treatment of the stenotic lesion in the body vessel. The distal protection device 10 is guided through the inner lumen preferably from the hub and distally beyond the balloon of the balloon catheter 42, exiting from the distal end 52 of the inner or balloon catheter 42 to a location within the vasculature downstream of the stenotic lesion.

In this embodiment, the apparatus further includes a polytetrafluoroethylene (PTFE) introducer sheath 64 for percutaneously introducing the wire guide 60 and the inner catheter 50 in a body vessel. Of course, any other suitable material may be used without falling beyond the scope or spirit of the present invention. The introducer sheath 64 may have any suitable size, e.g., between about three-french to eight-french. The introducer serves to allow the inner and balloon catheters to be percutaneously inserted to a desired location in the body vessel. The introducer sheath 64 receives the inner catheter 50 and provides stability to the inner catheter 50 at a desired location of the body vessel. For example, the introducer sheath 64 is held stationary within a common visceral artery, and adds stability to the inner catheter 50, as the inner catheter 50 is advanced through the introducer sheath 64 to a dilatation area in the vasculature.

When the distal end 52 of the inner catheter 50 is at a location downstream of the dilatation area in the body vessel, the balloon catheter 42 is inserted therethrough to the dilatation area. The device 10 is preferably loaded through the proximal end 54 of the balloon catheter 42 to a location therein adjacent the expandable balloon 46. The balloon catheter is then advanced through the inner lumen thereof for deployment through its distal end 52. In this embodiment, when the device is passed through the dilatation area, fluid (e.g. saline) may be passed through the proximal opening of the inflatable frame, providing rigidity therein to allow the device to be mechanically advanced or pushed through the balloon catheter. The fluid provides support and rigidity to the inflatable frame 12, placing the device 10 in its expanded state. In the expanded state, the inflatable frame 12 is configured to engage the wall of the body vessel, thereby opening the open end 24 of the filter 14 to capture emboli during angioplasty.

It is understood that the assembly described above is merely one example of an assembly that may be used to deploy the embolic protection device in the body vessel. Of course, other apparatus, assemblies and systems may be used to deploy any embodiment of the embolic protection device without falling beyond the scope or spirit of the present invention.

Figure 6:
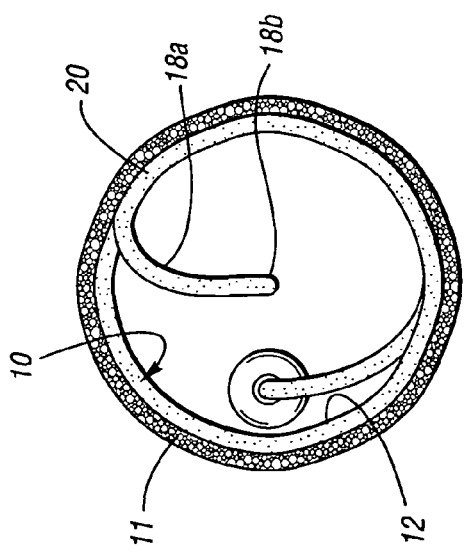
FIG. 6 is a flow chart of one method for capturing emboli during treatment of a stenotic lesion in a body vessel.

FIG. 6 illustrates a flow chart depicting one method 110 for capturing emboli during treatment of a stenotic lesion in a body vessel, implementing the assembly mentioned above. The method comprises percutaneously introducing a balloon catheter having an expandable balloon for angioplasty of the stenotic lesion in the body vessel in box 112. Introduction of the balloon catheter may be performed by any suitable means or mechanism. As mentioned above, an introducer sheath and a wire guide may be used to provide support and guidance to the balloon catheter. For example, the wire guide may be percutaneously inserted through the introducer sheath to the stenotic lesion in the body vessel. The balloon catheter may then be place over the wire guide for percutaneous guidance and introduction to the stenotic lesion.

The method 110 further comprises disposing the embolic protection device coaxially within the balloon catheter in box 114. The device may be disposed coaxially within the balloon catheter before or after percutaneous insertion of the balloon catheter. For example, once the balloon catheter is placed at the stenotic lesion, the wire guide may be removed therefrom, and the device may then be disposed within the balloon catheter for guidance and introduction in the body vessel. In this example, the expandable balloon is positioned at the stenotic lesion and the device, in its collapsed state, is disposed through the distal end of the balloon catheter downstream from the expandable balloon.

The method 110 further includes inflating the inflatable frame to the expanded state in box 116. Preferably, the inflatable frame is inflated prior to any dilatation, including predilatation, of the stenotic lesion. Upon inflation, proximal port of the device is placed in the closed position to restrict fluid exit therefrom, thereby maintaining the frame in the expanded state. In the expanded state, the open end of the filter is expanded to a proximally facing concave shape for capturing emboli during angioplasty.

The method may further include treating the stenotic lesion in the body vessel with the balloon catheter. In this example, the expandable balloon may be injected with saline and expanded for predilatation. As desired, additional balloon catheters may be used for primary and post-dilatation treatment of the stenotic lesion while the device is in its expanded state within the body vessel.

While the present invention has been described in terms of preferred embodiments, it will be understood, of course, that the invention is not limited thereto since modifications may be made to those skilled in the art, particularly in light of the foregoing teachings.

The invention claimed is:

1. An embolic protection device for capturing emboli during treatment of a stenotic lesion in a body vessel, the device comprising:
   an inflatable frame having a deployed state and an undeployed state, the inflatable frame including a proximal portion extending to a distal portion, the proximal portion defining a proximal opening in fluid communication with the distal portion for supplying fluid thereto, the distal portion having a predetermined shape and extending freely independent of any support member to a closed distal end when the inflatable frame is in the deployed state, the closed distal end being a free end independent of any support member connected thereto; and
   a filter attached to the inflatable frame for capturing emboli, the filter having a lip attached to the inflatable frame, a body extending distally from the lip, and a closed tail;
   wherein the distal portion of the inflatable frame extends toward the closed tail of the filter to the closed distal end.

2. The device of claim 1 wherein the inflatable frame is inflated in the deployed state and deflated in the undeployed state.

3. The device of claim 1 wherein the distal portion is made of shape memory material defining the predetermined shape when the inflatable frame is in the deployed state.

4. The device of claim 1 wherein the distal portion defines at least one helical portion when the inflatable frame is in the deployed state, the at least one helical portion having a helical configuration extending freely to the distal end.

5. The device of claim 1 wherein the distal portion defines a plurality of helical portions when the inflatable frame is in the deployed state, each having a helical configuration.

6. The device of claim 1 wherein the lip defines an open end of the filter when the inflatable frame is in the deployed state, the body is disposed about the inflatable frame, and the closed tail is positioned distally of the inflatable frame and configured to capture the emboli during treatment of the stenotic lesion.

7. The device of claim 1 wherein the filter comprises a net material for capturing emboli from the stenotic lesion.

8. An embolic protection assembly for capturing emboli during treatment of a stenotic lesion in a body vessel, the assembly comprising:
   a balloon catheter having a tubular body portion and an expandable balloon fluidly connected to the tubular body; and
   an embolic protection device at least partially coaxially disposed within the balloon catheter during treatment of the stenotic lesion in the body vessel, the embolic protection device comprising:
      an inflatable frame having a deployed state and an undeployed state, including a proximal portion extending to a distal portion, the proximal portion defining a proximal opening in fluid communication with the distal portion for supplying fluid thereto, the distal portion having a predetermined shape and extending freely independent of any support member to a closed distal end when the inflatable frame is in the deployed state, the closed distal end being a free end independent of any support member connected thereto; and
      a filter including a lip attached to the inflatable frame to define an open end of the filter when the inflatable frame is in the deployed state, a body extending from the lip and disposed about the inflatable frame, and a closed tail configured to capture the emboli during treatment of the stenotic lesion;
      wherein the distal portion of the inflatable frame extends toward the closed tail of the filter to the closed distal end.

9. The assembly of claim 8 wherein the inflatable frame is inflated in the deployed state and deflated in the undeployed state.

10. The assembly of claim 8 wherein the distal portion is made of shape memory material defining the predetermined shape when the inflatable frame is in the deployed state.

11. The assembly of claim 8 wherein the distal portion defines at least one helical portion when the inflatable frame is in the deployed state, the at least one helical portion having a helical configuration extending freely to the distal end.

12. The assembly of claim 8 wherein the distal portion defines a plurality of helical portions when the inflatable frame is in the deployed state, each having a helical configuration.

13. The assembly of claim 8 wherein the filter includes a lip attached to the inflatable frame to define an open end of the filter when the inflatable frame is in the deployed state, a body extending from the lip and disposed about the inflatable frame, and a closed tail positioned distally of the inflatable frame and configured to capture the emboli during treatment of the stenotic lesion.

14. The assembly of claim 8 wherein the filter comprises a net material for capturing emboli from the stenotic lesion.

15. The assembly of claim 8 further comprising:
   an inner catheter having a distal end through which the balloon catheter is disposed for deployment in the body vessel;
   a wire guide configured to be disposed through a lumen of the balloon catheter for percutaneous guidance through the body vessel; and
   an introducer sheath through which the inner catheter is inserted for percutaneous insertion to the body vessel.

16. The assembly of claim 15 wherein the inner catheter further includes a proximal end, the proximal end having a hub in fluid communication with the expandable balloon for inflation and deflation of the balloon.

* * * * *